United States Patent
Lindgren

(10) Patent No.: US 7,761,156 B2
(45) Date of Patent: Jul. 20, 2010

(54) METHOD FOR OPERATING AN IMPLANTABLE CARDIAC STIMULATOR TO SET THE ATRIAL STIMULATION TIME INTERVAL DEPENDENT ON THE EVOKED RESPONSE AMPLITUDE

(75) Inventor: Anders Lindgren, Täby (SE)

(73) Assignee: St. Jude Medical AB, Jarfalla (SE)

( * ) Notice: Subject to any disclaimer, the term of this patent is extended or adjusted under 35 U.S.C. 154(b) by 303 days.

(21) Appl. No.: 11/699,698

(22) Filed: Jan. 29, 2007

(65) Prior Publication Data

US 2007/0123942 A1    May 31, 2007

Related U.S. Application Data

(62) Division of application No. 10/870,402, filed on Jun. 17, 2004, now abandoned.

(30) Foreign Application Priority Data

Jun. 27, 2003    (SE)    .................... 0301919

(51) Int. Cl.
A61N 1/362    (2006.01)
(52) U.S. Cl. .............. 607/14; 607/9; 607/17; 607/25; 607/27; 607/28
(58) Field of Classification Search ............ 607/9, 607/14, 17, 25, 27–28
See application file for complete search history.

(56) References Cited

U.S. PATENT DOCUMENTS

| | | | |
|---|---|---|---|
| 4,969,461 A | 11/1990 | Callaghan et al. |
| 5,184,615 A | 2/1993 | Nappholz et al. |
| 5,271,394 A | 12/1993 | Girodo et al. |
| 5,395,397 A | 3/1995 | Lindgren et al. |
| 5,626,620 A | 5/1997 | Kieval et al. |
| 5,713,929 A | 2/1998 | Hess et al. |
| 6,442,429 B1 | 8/2002 | Hill et al. |
| 6,510,342 B1 | 1/2003 | Park et al. |

(Continued)

FOREIGN PATENT DOCUMENTS

EP    0 318 304    5/1989

OTHER PUBLICATIONS

"AF Suppression Algorithm: A New Tool for Reducing Atrial Fibrillation in Pacemaker Recipients," St. Jude Medical Cardiac Rhythm Management Division (2001).

*Primary Examiner*—Carl H Layno
*Assistant Examiner*—Deborah Malamud
(74) *Attorney, Agent, or Firm*—Schiff Hardin LLP

(57) ABSTRACT

In a method for operating an implantable heart stimulating device with atrial overdrive capability having an atrial stimulation unit for stimulating the atrium via stimulation electrode(s), an atrial evoked response detector determines an atrial evoked response amplitude, and an atrial control unit controls an atrial timing unit to set an atrial stimulation time interval length between consecutively applied atrial stimulation pulses. The atrial stimulation time interval length is set in dependent on the determined atrial evoked response amplitude such that the next time interval length is a predetermined percentage of the present time interval length. If the ER signal amplitude decreases, the stimulating interval has to be decreased. The control unit can also try to increase the stimulating interval back to back until a decrease in ER signal amplitude is seen in order to avoid too high stimulating rate.

7 Claims, 3 Drawing Sheets

U.S. PATENT DOCUMENTS

| | | |
|---|---|---|
| 6,850,800 B1 | 2/2005 | Uhrenius et al. |
| 6,952,609 B1 | 10/2005 | Lindgren |
| 2003/0100923 A1 | 5/2003 | Bjorling et al. |
| 2003/0153955 A1 | 8/2003 | Park et al. |
| 2003/0229380 A1 | 12/2003 | Adams et al. |
| 2004/0260350 A1 | 12/2004 | Brandstetter et al. |

METHOD FOR OPERATING AN IMPLANTABLE CARDIAC STIMULATOR TO SET THE ATRIAL STIMULATION TIME INTERVAL DEPENDENT ON THE EVOKED RESPONSE AMPLITUDE

RELATED APPLICATION

The present application is a division of Ser. No. 10/870,402, filed Jun. 17, 2004 now abandoned.

BACKGROUND OF THE INVENTION

1. Field of the Invention

The present invention relates to a method for operating an implantable cardiac stimulator of the type having atrial overdrive capability, and having an atrial stimulator for stimulating the atrium via stimulation electrode(s), an atrial evoked response detector for determining an atrial evoked response amplitude, and an atrial control unit that controls an atrial timer to set an atrial stimulation time interval length between consecutive atrial stimulation pulses.

2. Description of the Prior Art

A healthy heart pumps blood through the circulatory system in successive, periodic cycles each including an atrial contraction followed shortly thereafter by a ventricular contraction. The successive atrial and ventricular contractions occur upon being triggered by the heart's natural pacemaker, which causes electrical wave fronts to propagate through cardiac tissue, causing the tissue cells to be momentarily depolarized, thereby initiating the contractions. If a patient's natural pacemaker, through disease, ceases to function or functions only erratically, artificial pacing therapy can be provided by an implanted pacemaker, which delivers low-energy pacing pulses to the atrium, or to the ventricle, or to both the atrium and the ventricle in a properly synchronized sequence. Depending on the needs of a particular patient, the pacemaker can be programmed to continuously supply such pacing pulses without interruption, or can operate to sense when the patient's natural pacemaker has failed to deliver a signal resulting in contraction, and only then does the implanted pacemaker deliver a pacing pulse. Pacemakers of this latter type are known as demand pacemakers.

Fibrillation, in general, characterizes abnormal operation of the heart, which can spontaneously occur, wherein the normal initiation of the electrical wave fronts becomes chaotic and therefore the cardiac tissue never receives a clear or coherent signal triggering contraction, and pumping therefore ceases. Ventricular fibrillation is a life-threatening condition, and when it occurs must be treated rapidly and effectively. For this purpose, implantable defibrillators are well-known in the art, which deliver one or more high-energy electrical pulses to the cardiac tissue, at selected locations and in a selected timing sequence, so as to momentarily depolarize substantially all of the cardiac tissue, thereby rendering virtually all of the cardiac tissue momentarily unable to propagate the chaotic wave fronts. If defibrillation is successful, when the cells again become capable of propagating a pacing wave front, they will do so in a normal, non-chaotic manner.

Atrial fibrillation is usually not an immediately life-threatening pathology, and can be tolerated for a certain amount of time without significant adverse consequences to the patient. This means that upon the occurrence of atrial fibrillation, there is usually a relatively long time during which an effective therapy can be developed, and subsequently administered. Although implantable defibrillator technology, primarily intended for treating ventricular fibrillation, can be adapted also to treat atrial fibrillation, the delivery of high energy shocks to the patient is painful and moreover, such drastic therapy is usually not necessary in the case of atrial fibrillation. Atrial fibrillation is also treated by extracorporeal delivery of the shocks to the heart through the skin of the patient by an external defibrillator of the type well-known in the art, also being extremely uncomfortable for the patient. Moreover, this type of treatment generally results only in temporary relief for patients, and must be repeated.

In treating atrial fibrillation by means of electrical shocks supplied to the heart, such shocks must be applied in synchronism with the ventricular electrical activity, otherwise ventricular fibrillation may be induced.

Another treatment regimen for atrial fibrillation is the administration of suitable drugs for reducing the occurrences of atrial fibrillation. Drugs suitable for this purpose which are currently available, however, have many undesirable side effects, and many patients become resistant to their atrial fibrillation suppressing properties, thereby significantly reducing the therapeutic effect of such drugs.

Recent pacemakers include an overdrive capability adapted to control the mechanisms responsible for atrial fibrillation (AF). Herein, overdrive is defined as a pacing regime that suppresses the initiation of atrial fibrillation by stimulating the atrium at a rate higher than the patient's own intrinsic atrial rate. St Jude Medical has designed an AF suppression algorithm, known as the Dynamic Atrial Overdrive (DAO) algorithm for that purpose, see e.g. the brochure "AF Suppression Algorithm: A New Tool for Reducing Atrial Fibrillation in Pacemaker Recipients" © 2001 St Jude Medical Cardiac Rhythm Management Division. It accomplishes this by continually monitoring the intrinsic atrial rhythm, promptly increasing the stimulation rate when the intrinsic atrial rhythm emerges, and periodically reducing the stimulation rate gradually to search for intrinsic atrial activity. This process ensures that the stimulation rate is not inappropriately rapid when the patient is at rest, yet is sufficiently high when the patient is active.

With AF suppression turned on, detection of two intrinsic atrial events within a 16-cycle window causes an increase in the atrial stimulation rate. The magnitude of the increase depends among others on the current stimulation rate. The increased rate is maintained for a programmed number of overdrive cycles, after which the system begins to search for the intrinsic rate by gradually extending the atrial stimulation interval (8 ms for rates >100 ppm; 12 ms for rates <100 ppm).

The described algorithm is illustrated by the ECG shown in FIG. 1. In FIG. 1, while overdrive pacing the atrium at a rate of 84 ppm, the device detects two intrinsic atrial events and immediately responds with a rate increase (by overdrive pacing at a rate of 93 ppm). After stimulating the atrium for the selected number of overdrive pacing cycles (15 cycles at a rate of 93 ppm), the device begins to extend the pacing cycle lengths to search for intrinsic atrial activity (rate recovery). Detection of two intrinsic atrial events would again initiate a prompt rate increase and reset the cycle length counter.

In the presently used AF suppression algorithm, which briefly has been described above, the paced atrial rate is decreased until two spontaneous P-waves are seen within a 16-cycle window. The algorithm then increases the paced atrial rate to regain a paced atrial rhythm, where after it again starts to decrease its pace rate until two spontaneous P-waves are seen within a 16-cycle window.

SUMMARY OF THE INVENTION

Thus, in some cases spontaneous P-waves interrupt the AF suppression algorithm at regular intervals, and an object of the present invention is to further improve the algorithm so that the paced atrial rhythm is maintained and not interrupted by spontaneous sinus rhythm.

Thus, the object is generally achieved by monitoring the changes of the atrial evoked response (ER) signal amplitudes. It has been observed that the ER signal amplitude decreases by increased degree of atrial fusion (and the amplitude will vanish completely during atrial inhibition.)

Atrial fusion is herein defined as the ECG waveform that typically results when an intrinsic atrial depolarization and an atrial stimulation pulse occur simultaneously and both contribute to the electrical activation of the atrium.

This change in the amplitude is used to set the atrial stimulation time interval length in dependence of the determined atrial evoked response amplitude such that said time interval length is a predetermined percentage of an intrinsic atrial time interval length.

The pacemaker tries to keep the paced atrial intervals as long as possible. However, if a decreasing ER signal amplitude is seen, this indicates that the atrial pacing interval is becoming too long and thus has to be decreased somewhat to maintain a paced atrial rhythm. The pacemaker can also try to increase the stimulating intervals until a decrease in ER signal amplitude is seen.

DESCRIPTION OF THE PREFERRED EMBODIMENTS

Figure 1:
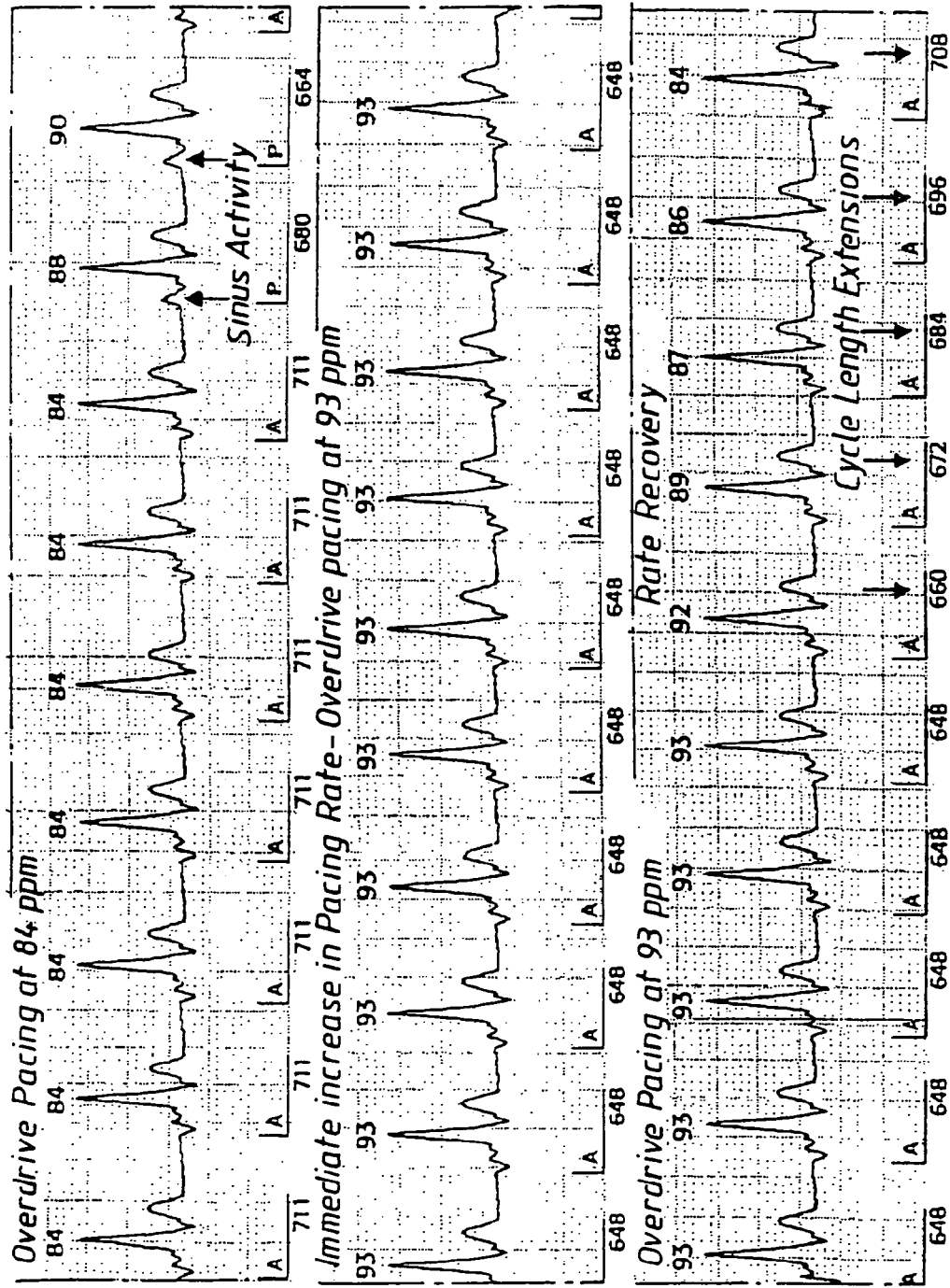
FIG. 1 shows an ECG that illustrates the conventional AF suppression algorithm.
Figure 2:
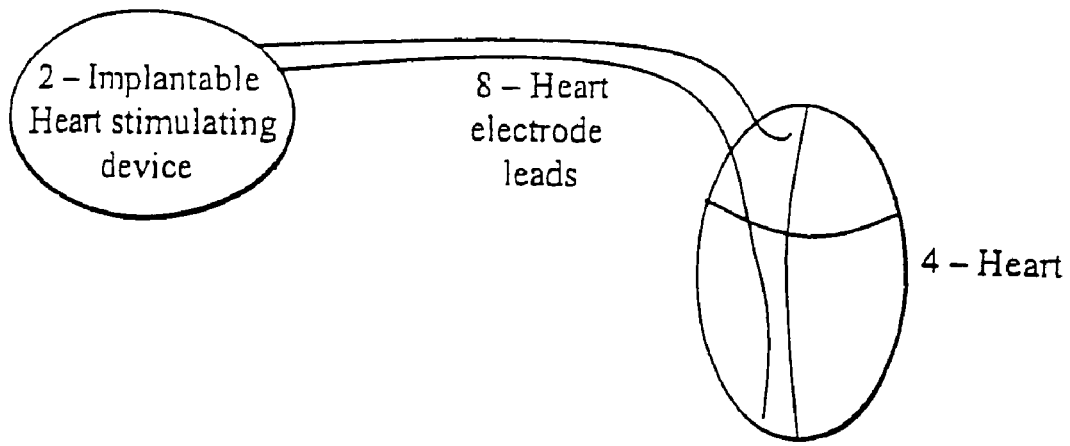
FIG. 2 is a schematic illustration of an implantable heart stimulating device operable in accordance with the inventive method.

FIG. 2 shows a schematic illustration of an implantable heart stimulating device where the present invention is applicable. The heart stimulating device 2 is provided with two heart electrode leads 8 inserted into the heart 4. One of the electrode leads is inserted into the right atrium and one is inserted into the right ventricle for applying stimulation pulses to the respective heart chambers. This is standard implantation locations in a dual chamber pacemaker. The present invention is naturally also applicable when using alternative placements of the heart electrodes. This may be, for example, epicardial placements or locations in the coronary veins, or in both atria, in both single (AAI) or dual chamber pacemakers.

Figure 3:
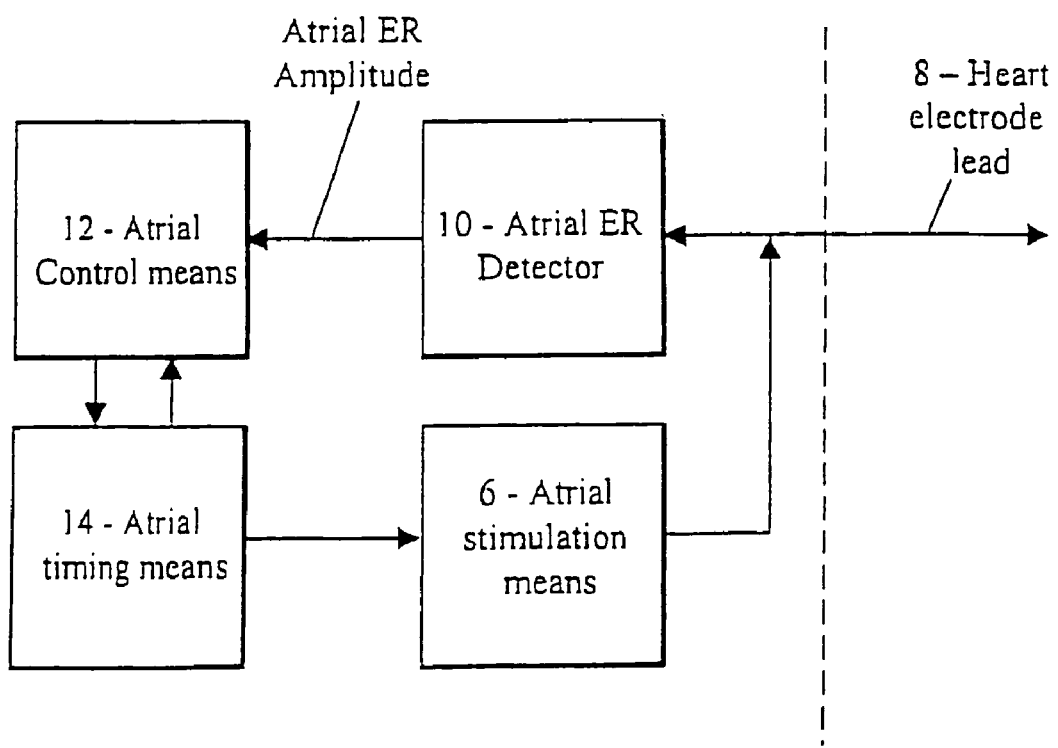
FIG. 3 is a block diagram illustrating the present invention.

FIG. 3 is a block diagram illustrating the present invention. Only components relevant for describing the present invention are shown. Also included (but not shown) in a conventional pacemaker are e.g. corresponding circuitry for the ventricle channel, a ventricular electrode lead and power supply means.

As shown in FIG. 3 the implantable heart stimulating device 2, provided with an atrial overdrive capability, has an atrial stimulation means 6 for stimulating the atrium via stimulation electrode(s) arranged at the distal end of an atrial heart electrode lead 8, an atrial evoked response (ER) detector 10 adapted to determine an atrial evoked response amplitude and an atrial control unit 12 to control an atrial timing unit 14 to set an atrial stimulation time interval length between consecutively applied atrial stimulation pulses. The atrial evoked response amplitude preferably is determined as the amplitude of the electrical evoked response signal.

The atrial stimulation time interval length is set dependent on the determined atrial evoked response amplitude such that the next time interval length is a predetermined percentage of the present time interval length. Preferably, the predetermined percentage is, when the interval is to be decreased, in the interval 80-95% and may be set by an external programming means (not shown) in steps of 5%.

In general, the atrial stimulation time interval length is set as long as possible in relation to an intrinsic atrial time interval length.

Figure 4:
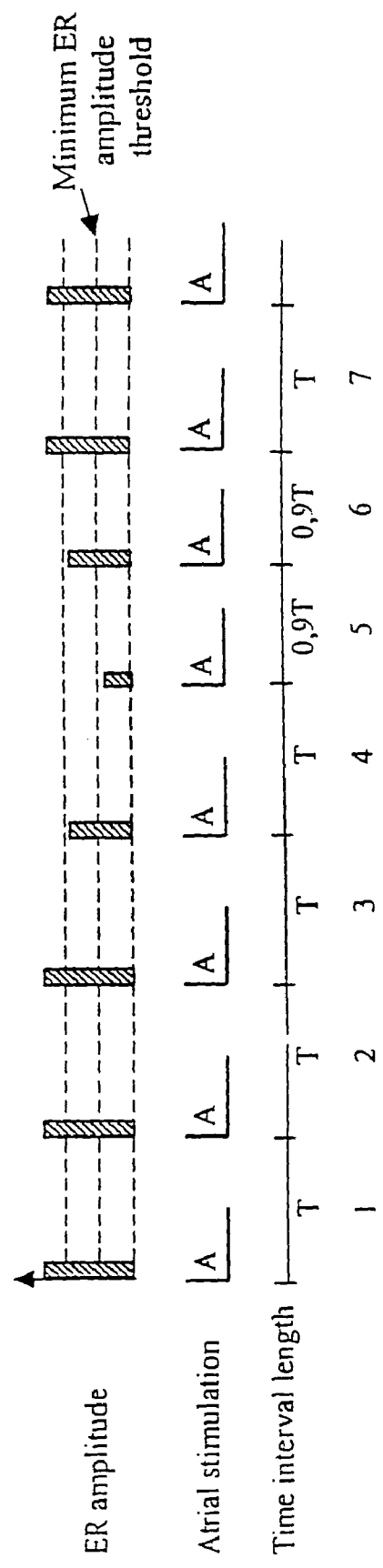
FIG. 4 is a simplified chart of a number of heart cycles showing the relationship of the determined ER amplitude and the atrial stimulation time interval length according to the present invention.

FIG. 4 is a simplified chart of a number of heart cycles showing the relationship of the determined ER amplitude and the atrial stimulation time interval length according to the present invention. Atrial stimulation pulses are indicated by an "A".

FIG. 4 heart cycles 1-4 all have the same interval length T. The ER amplitude is sensed by the atrial electrode, measured by the atrial ER detector 10 and a measure of the amplitude is supplied to the atrial control unit 12. These ER amplitude measures are indicated in FIG. 4 as vertical bars. In the atrial control unit 12 the ER amplitude measure is compared to thresholds in order to determine if the ER amplitude is increasing or decreasing and also to determine if the ER amplitude is less than a minimum ER threshold amplitude.

As can be seen from FIG. 4 the ER amplitude in heart cycle 4 is smaller than the previous ER amplitude and in heart cycle 5 the ER amplitude is less than the minimum ER amplitude threshold. The time interval length is then shortened a predetermined percentage of the present time interval length, in FIG. 4 by 10%.

The shortened time interval length is kept until the ER amplitude increases again and then the time interval length is returned, e.g. to its previous length. In the figure the short time interval length is kept for two heart cycles and is prolonged when the ER amplitude is above a higher threshold.

As known to those skilled in the art the time interval length may be decreased and increased in many different ways. In this case the short time interval is kept for one heart cycle despite the ER amplitude in heart cycle 6 is greater than the minimum ER amplitude threshold. The return to the longer time interval may naturally be instant or the shorter time interval may be kept for a larger number of heart cycles.

The time interval changes may be in one step, as in the illustrated example, or be more gradual over a number of heart cycles under direct control of any detected changes of the ER amplitudes.

As illustrated by FIG. 4, if said atrial stimulation time interval length was decreased in any of a predetermined number of preceding heart cycles (4 and 5) and the evoked response amplitude is above the minimum ER amplitude threshold, the atrial stimulation time interval length is increased (in heart cycle 7) under control of the control unit 12.

It should be understood that the present invention is primarily intended to be fully incorporated in the presently used AF suppression algorithm designed by St Jude Medical.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating an implantable cardiac stimulator having an atrial pulse generator, comprising the steps of:
   operating said pulse generator in a pacing regimen and, in said pacing regimen, delivering stimulation pulses in vivo from the atrial pulse generator to an atrium of a heart with a set, current stimulation time interval length between consecutive stimulation pulses;
   measuring a degree of atrial fusion in the atrium of the heart by making an in vivo measurement of an amplitude of an atrial evoked response for at least one of the delivered stimulation pulses, thereby obtaining a measured amplitude;
   in a processor, automatically comparing said measured amplitude to an amplitude threshold to determine whether said measured amplitude has a relation to said amplitude threshold that deviates from a predetermined relationship that is indicative of atrial fusion not being present;
   when said relationship of said measured amplitude to said amplitude threshold deviates from said predetermined relationship, using the deviation as an indication that atrial fusion exists and automatically changing operation of said atrial pulse generator from said pacing regimen to emit consecutive stimulation pulses in an overdrive regimen and, in said overdrive regimen, automatically re-setting the atrial stimulation time interval length to a length that prevents said atrial fusion, dependent on said deviation from said predetermined relationship, as a predetermined percentage of said current time interval length; and
   from said processor, maintaining said atrial pulse generator as operating in said overdrive regimen until said measured amplitude and said threshold amplitude no longer exhibit said deviation from said predetermined relationship.

2. A method as claimed in claim 1 comprising setting said atrial stimulation time interval for a next time interval length in a range between 85% and 95%, as said predetermined percentage.

3. A method as claimed in claim 1 comprising, in said processor identifying a time interval length intrinsic to the atrium and setting said time interval length for said next time interval to be as long as possible with respect to the time interval length intrinsic to the atrium.

4. A method as claimed in claim 1 comprising automatically comparing said measured amplitude to a plurality of amplitude thresholds to identify a decrease of said measured amplitude, and decreasing said atrial stimulation time interval length for said next time interval if a decreasing measured amplitude is identified.

5. A method as claimed in claim 1 comprising automatically determining if said measured amplitude is less than a minimum evoked response amplitude threshold and, if so, decreasing said atrial stimulation time interval length for said next time interval by said predetermined percentage.

6. A method as claimed in claim 1 comprising automatically comparing said measured amplitude to a plurality of amplitude thresholds to identify an increase of said measured amplitude, and increasing said atrial stimulation time interval length for said next time interval length by said predetermined percentage if an increasing measured amplitude is identified.

7. A method as claimed in claim 1 comprising comparing said measured amplitude to a plurality of different amplitude thresholds to identify a decreasing measured amplitude, and decreasing said atrial stimulation time interval length for said next time interval by said predetermined percentage if a decreasing measured amplitude is identified and, if said atrial stimulation time interval length for said next time interval was decreased in any of a predetermined number of preceding heart cycles, and if said measured amplitude is above a predetermined threshold, increasing said atrial stimulation time interval length for said next time interval length.

* * * * *